: US008286500B2

United States Patent
Hsu et al.

(10) Patent No.: US 8,286,500 B2
(45) Date of Patent: Oct. 16, 2012

(54) TESTING DEVICE AND LIMITING SWITCH THEREOF

(75) Inventors: Nai-Ren Hsu, Taipei (TW); Pao-Hua Tai, Taipei (TW); Yen-Chih Chen, Taipei (TW); Pei-Fen Liu, Taipei (TW)

(73) Assignee: Inventec Corporation, Taipei (TW)

( * ) Notice: Subject to any disclaimer, the term of this patent is extended or adjusted under 35 U.S.C. 154(b) by 280 days.

(21) Appl. No.: 12/844,101

(22) Filed: Jul. 27, 2010

(65) Prior Publication Data

US 2011/0239776 A1 Oct. 6, 2011

(30) Foreign Application Priority Data

Apr. 6, 2010 (TW) .............................. 99110566 A

(51) Int. Cl.
*G01N 3/02* (2006.01)
(52) U.S. Cl. ........................................... 73/856; 73/798
(58) Field of Classification Search .................. None
See application file for complete search history.

(56) References Cited

U.S. PATENT DOCUMENTS

| 4,628,741 | A | * | 12/1986 | Cable ............................... 73/826 |
| 2004/0065155 | A1 | * | 4/2004 | Liu et al. ........................ 73/798 |
| 2010/0051344 | A1 | * | 3/2010 | Chen ............................. 174/377 |

FOREIGN PATENT DOCUMENTS

| TW | 145374 | 2/1990 |
| TW | I235396 | 7/2005 |

\* cited by examiner

*Primary Examiner* — Andre Allen
(74) *Attorney, Agent, or Firm* — J.C. Patents

(57) ABSTRACT

A limiting switch suitable for a testing device is provided. The testing device includes a fixed frame and a clamping element pivoted to each other. The limiting switch includes a first rod, a second rod, a first switching element and a second switching element. The first and second rods are fixed to the clamping element. The first and second switching elements are pivotally connected to the fixed frame. When the clamping element is pivoted along a first direction, the second rod pushes the second switching element to pivot and the first rod is moved to contact with the first switching element. When the clamping element is pivoted along a second direction opposite to the first direction, the first rod pushes the first switching element to pivot and the second rod is moved to contact with the second switching element.

20 Claims, 7 Drawing Sheets

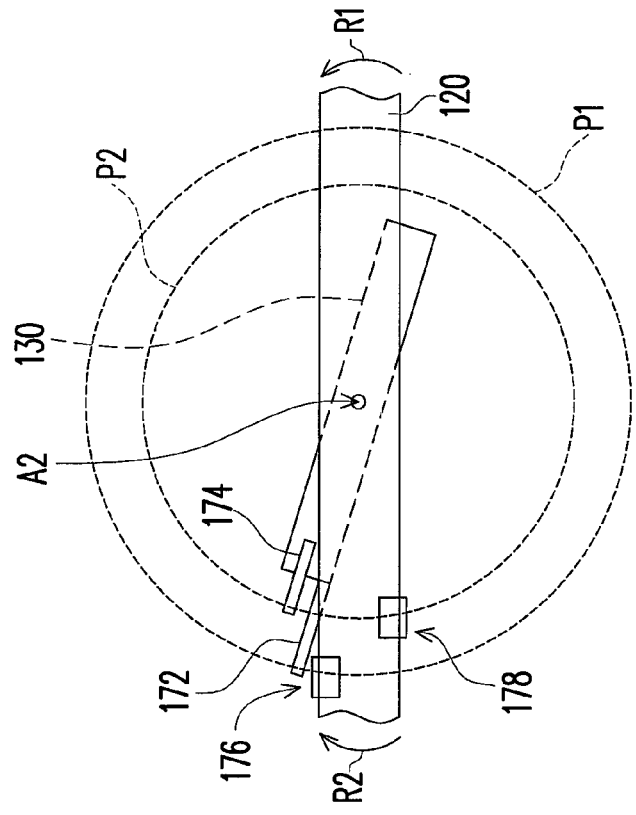
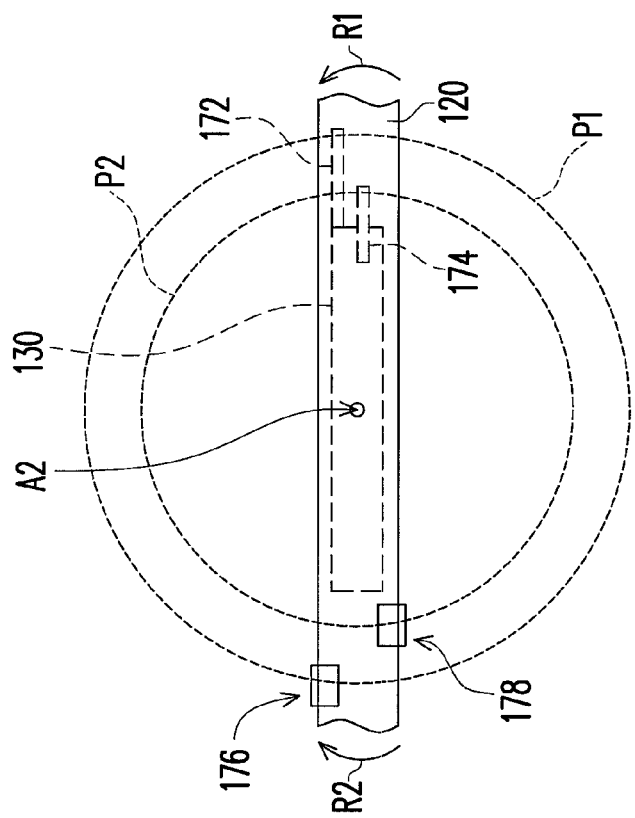
FIG. 3B
FIG. 3A

TESTING DEVICE AND LIMITING SWITCH THEREOF

CROSS-REFERENCE TO RELATED APPLICATION

This application claims the priority benefit of Taiwan application serial no. 99110566, filed Apr. 6, 2010. The entirety of the above-mentioned patent application is hereby incorporated by reference herein and made a part of this specification.

BACKGROUND

1. Field of the Invention

The present invention relates to a testing device and a limiting switch thereof. More particularly, the present invention relates to a testing device and a limiting switch thereof for detecting rotation times that can be born by a shaft of a folding-type electronic device.

2. Description of Related Art

With development of electronic technology, electronic products in the market are continually developed in order to cope with consumer's requirements of lightness, slimness and high efficiency, and various folding-type electronic devices such as notebook computers, cell phones and personal digital assistants (PDAs) have become popular in the market.

A general folding-type electronic device is mainly consisted of a flat display screen and a host, and the display screen and the host are connected through a single shaft, so that the display screen can be pivoted relative to the host for being opened or closed. To ensure a long-term usage, the shaft of the electronic device is designed to be capable of bearing repeatedly opening and closing actions. Therefore, a conventional technique provides a testing device for testing the shaft of the electronic device. The testing device can simulate user's actions of opening and closing the electronic device, and can repeatedly execute such actions to test whether the shaft can bear enough times of the opening and closing actions, or test a damage situation of the shaft when the action times exceeds a limit. However, during the test process, if a pivoted angle is excessive, the shaft of the folding-type electronic device can be damaged.

The Taiwan. patent No. I235396 discloses a one-axis type rotating switch. In addition, the Taiwan. patent No. 145374 also discloses a one-axis type rotating switch.

SUMMARY

The invention is directed to a testing device for testing rotation times that can be born by a shaft of a folding-type electronic device, which can be used to avoid a damage of the shaft of the folding-type electronic device caused by an excessive pivoted angle during a testing process.

The invention provides a testing device adapted to test an electronic device. The electronic device has a first body and a second body, and the first body is suitable for rotating relative to the second body. The testing device includes a carrier platform, a fixed frame, a clamping element and a limiting switch. The carrier platform is used for carrying the first body. The fixed frame is pivotally connected to the carrier platform. The clamping element is pivotally connected to the fixed frame, and is used for clamping the second body. The limiting switch includes a first rod, a second rod, a first switching element and a second switching element. The first rod is fixed to the clamping element. The second rod is fixed to the clamping element. The first switching element is pivotally connected to the fixed frame and is located on a first moving path. The second switching element is pivotally connected to the fixed frame and is located on a second moving path. When the clamping element is pivoted relative to the fixed frame along a first direction, the second switching element is pushed by the second rod to pivot relative to the fixed frame and move away from the second moving path, and the first rod is moved along the first moving path to contact with the first switching element. When the clamping element is pivoted relative to the fixed frame along a second direction opposite to the first direction, the first switching element is pushed by the first rod to pivot relative to the fixed frame and move away from the first moving path, and the second rod is moved along the second moving path to contact with the second switching element.

In an exemplary embodiment of the invention, the testing device further includes a first driving device and a second driving device. The first driving device is disposed between the carrier platform and the fixed frame for driving the fixed frame to pivot relative to the carrier platform. The second driving device is disposed between the clamping element and the fixed frame for driving the clamping element to pivot relative to the fixed frame.

In an exemplary embodiment of the invention, the testing device further includes a first shaft sensor, a second shaft sensor and a control unit. The first shaft sensor is disposed between the carrier platform and the fixed frame for sensing a first pivoted angle of the fixed frame relative to the carrier platform. The second shaft sensor is disposed between the clamping element and the fixed frame for sensing a second pivoted angle of the clamping element relative to the fixed frame. The control unit is coupled to the first driving device, the second driving device, the first shaft sensor and the second shaft sensor, and the control unit is used for controlling the first driving device and the second driving device according to the first pivoted angle and the second pivoted angle.

In an exemplary embodiment of the invention, the control unit is coupled to the first switching element and the second switching element, wherein when the first rod contacts with the first switching element, the first switching element outputs a first switch signal to the control unit for stopping an action of the first driving device, and when the second rod contacts with the second switching element, the second switching element outputs a second switch signal to the control unit for stopping an action of the first driving device.

In an exemplary embodiment of the invention, the testing device further includes two couplings flexibly connected to the first driving device and the second driving device, respectively.

In an exemplary embodiment of the invention, the clamping element includes a support frame and a plurality of clamps. The support frame is pivotally connected to the fixed frame. The clamps are connected to the support frame for clamping the second body.

In an exemplary embodiment of the invention, the support frame includes a frame body and a lifter. The frame body is pivotally connected to the fixed frame. The lifter is liftably disposed on the frame body, and the clamps are connected to the lifter.

In an exemplary embodiment of the invention, the clamps are axially disposed on the support frame, and the clamping element further includes a plurality of elastic elements disposed on the clamps for exerting an elastic force to the second body through the clamps.

In an exemplary embodiment of the invention, the testing device further includes a plurality of fixing elements detachably connected between the fixed frame and the clamping element for limiting a pivotal rotation of the clamping element relative to the fixed frame.

In an exemplary embodiment of the invention, the fixing elements are screws.

In an exemplary embodiment of the invention, the fixed frame is pivotally connected to the carrier platform along a first axis, the clamping element is pivotally connected to the fixed frame along a second axis, and the first axis is substantially perpendicular to the second axis.

In an exemplary embodiment of the invention, an extending direction of the first rod and an extending direction of the second rod are substantially perpendicular to the second axis, a distance between a free end of the first rod and the second axis is greater than a distance between a free end of the second rod and the second axis, and a distance between the first switching element and the second axis is greater than a distance between the second switching element and the second axis.

The invention provides a limiting switch adapted to a testing device. The testing device includes a carrier platform, a fixed frame and a clamping element. The fixed frame is pivotally connected to the carrier platform, and the clamping element is pivotally connected to the fixed frame. The limiting switch includes a first rod, a second rod, a first switching element and a second switching element. The first rod is fixed to the clamping element. The second rod is fixed to the clamping element. The first switching element is pivotally connected to the fixed frame and is located on a first moving path. The second switching element is pivotally connected to the fixed frame and is located on a second moving path. When the clamping element is pivoted relative to the fixed frame along a first direction, the second switching element is pushed by the second rod to pivot relative to the fixed frame and move away from the second moving path, and the first rod is moved along the first moving path to contact with the first switching element. When the clamping element is pivoted relative to the fixed frame along a second direction opposite to the first direction, the first switching element is pushed by the first rod to pivot relative to the fixed frame and move away from the first moving path, and the second rod is moved along the second moving path to contact with the second switching element.

A control unit of the testing device is coupled to the first switching element and the second switching element, wherein when the first rod contacts with the first switching element, the first switching element outputs a first switch signal to the control unit for stopping an action of the first driving device, and when the second rod contacts with the second switching element, the second switching element outputs a second switch signal to the control unit for stopping an action of the first driving device.

In an exemplary embodiment of the invention, the fixed frame is pivotally connected to the carrier platform along a first axis, the clamping element is pivotally connected to the fixed frame along a second axis, and the first axis is substantially perpendicular to the second axis. An extending direction of the first rod and an extending direction of the second rod are substantially perpendicular to the second axis, a distance between a free end of the first rod and the second axis is greater than a distance between a free end of the second rod and the second axis, and a distance between the first switching element and the second axis is greater than a distance between the second switching element and the second axis.

In an exemplary embodiment of the invention, the first axis and the second axis define a plane, a distance between an orthogonal projection of the first rod on the plane and the first axis is less than a distance between an orthogonal projection of the second rod on the plane and the first axis, and a distance between an orthogonal projection of a free end of the first switching element on the plane and the first axis is less than a distance between an orthogonal projection of a free end of the second switching element on the plane and the first axis.

In an exemplary embodiment of the invention, the fixed frame has a first blocking wall corresponding to the first switching element, and after the first rod moves along the first moving path to contact with the first switching element, the first rod continually moves along the first moving path to push the first switching element to pivot relative to the fixed frame for contacting with the first blocking wall.

In an exemplary embodiment of the invention, the fixed frame has a second blocking wall corresponding to the second switching element, and after the second rod moves along the second moving path to contact with the second switching element, the second rod continually moves along the second moving path to push the second switching element to pivot relative to the fixed frame for contacting with the second blocking wall.

In an exemplary embodiment of the invention, the testing device further includes a first torsion spring connected to the fixed frame and the first switching element for providing a torque to restore the first switching element pivoted relative to the fixed frame back to the first moving path.

In an exemplary embodiment of the invention, the testing device further includes a second torsion spring connected to the fixed frame and the second switching element for providing a torque to restore the second switching element pivoted relative to the fixed frame back to the second moving path.

According to the above descriptions, during the testing process of the testing device of the invention, the operation of the testing device can be stopped through a contact between the first rod and the first switching element of the limiting switch or a contact between the second rod and the second switching element, so as to avoid a damage of the shaft of the folding-type electronic device caused by excessive pivoted angle during the testing process. Moreover, the first switching element and the second switching element are pivotally connected to the fixed frame. In this way, when the first rod cannot be moved to contact the first switching element due to that the second switching element blocks the second rod, the second rod can temporarily push away the second switching element, so that the first rod can be moved to contact with the first switching element. Similarly, when the second rod cannot be moved to contact the second switching element due to that the first switching element blocks the first rod, the first rod can temporarily push away the first switching element, so that the second rod can be moved to contact with the second switching element.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 3A-3C are diagrams illustrating partial actions of a testing device of FIG. 1 viewing from a viewing direction V1.

DETAILED DESCRIPTION OF DISCLOSED EMBODIMENTS

Figure 1:
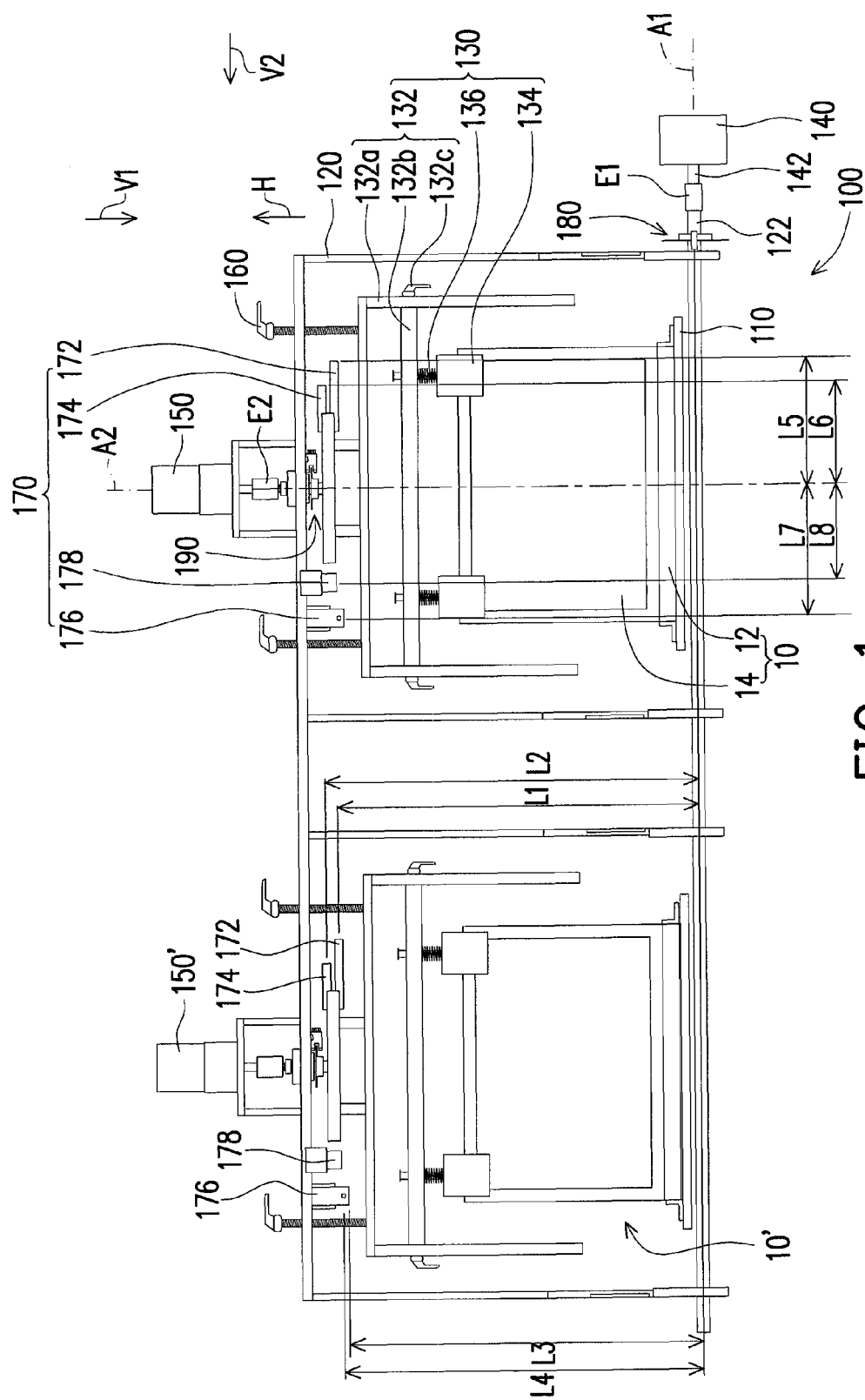
FIG. 1 is a front view of a testing device testing a folding-type electronic device according to an exemplary embodiment of the invention.
Figure 2:
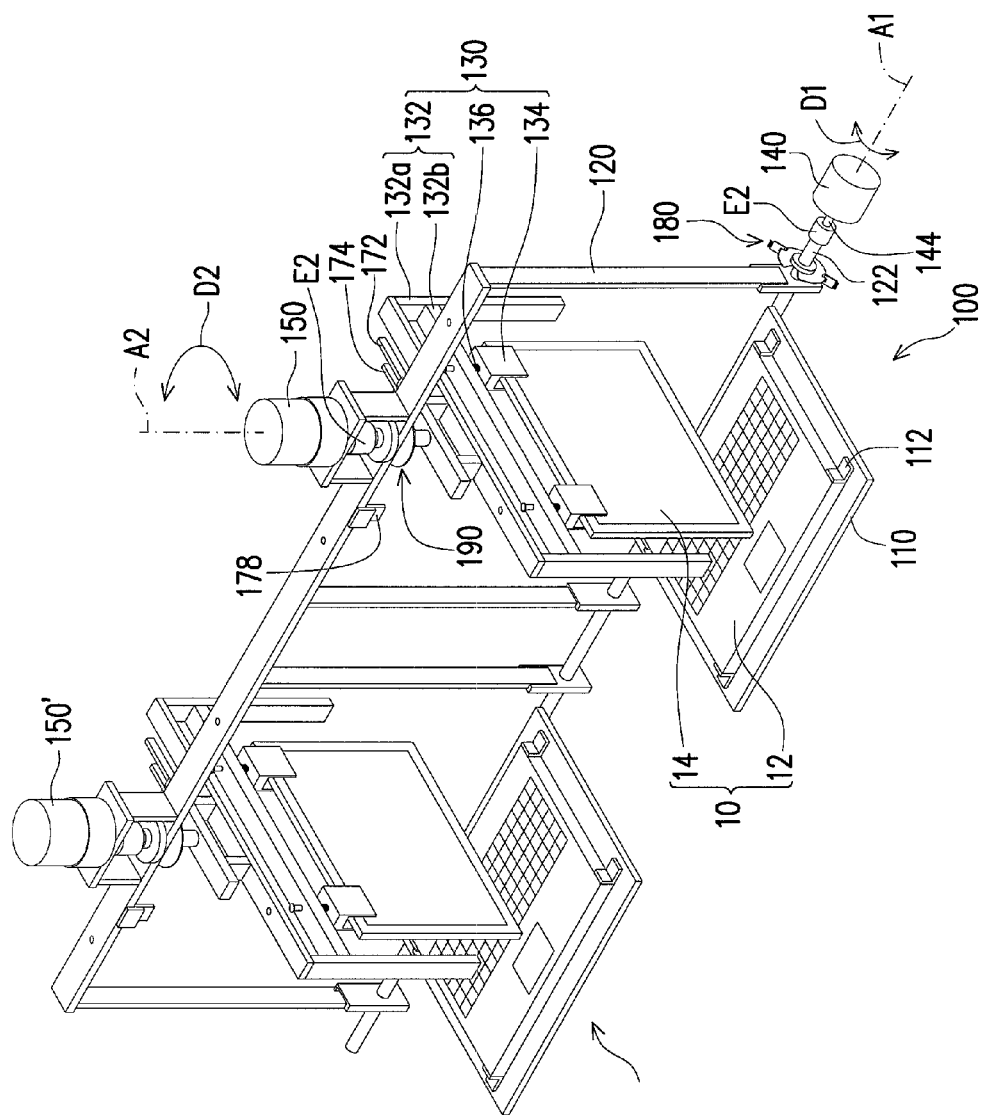
FIG. 2 is a three-dimensional view of a testing device of FIG. 1 turning over a second body of a folding-type electronic device.

FIG. 1 is a front view of a testing device testing a folding-type electronic device according to an exemplary embodiment of the invention. FIG. 2 is a three-dimensional view of a testing device of FIG. 1 turning over a second body of the folding-type electronic device. Referring to FIG. 1 and FIG. 2, the testing device 100 is adapted to perform a rotation test of opening and closing a folding-type electronic device 10. The folding-type electronic device 10 is, for example, a notebook computer, which includes a first body 12, a second body 14 and a shaft (not shown). The first body 12 is, for example, a host of the notebook computer, and the second body 14 is, for example, a display screen of the notebook computer. The shaft is connected between the first body 12 and the second body 14, so that the second body 14 can be opened or turned over relative to the first body 12 through the shaft.

The testing device 100 includes a carrier platform 110, a fixed frame 120, a clamping element 130, a first driving device 140 and a second driving device 150. The carrier platform 110 is used for carrying the first body 12. In the present exemplary embodiment, the carrier platform 110 may have a plurality of position-limiting elements 112 located around the first body 12 for limiting a position of the first body 12 relative to the carrier platform 110. The fixed frame 120 is pivotally connected to the carrier platform 110. The clamping element 130 is pivotally connected to the fixed frame 120, and is used for clamping the second body 14. In the present exemplary embodiment, the fixed frame 120 is pivotally connected to the carrier platform 110 along a first axis A1, and the clamping element 130 is pivotally connected to the fixed frame 120 along a second axis A2, wherein the first axis A1 is substantially perpendicular to the second axis A2.

The first driving device 140 is disposed between the carrier platform 110 and the fixed frame 120 for driving the fixed frame 120 to pivot relative to the carrier platform 110. The second driving device 150 is disposed between the clamping element 130 and the fixed frame 120 for driving the clamping element 130 to pivot relative to the fixed frame 120. In the present exemplary embodiment, the first driving device 140 and the second driving device 150 are, for example, motors or pneumatic cylinders, which are respectively used for providing a driving force.

When the first driving device 140 drives the fixed frame 120 to pivot along a direction D1, the second body 140 is opened or closed relative to the first body 12. When the second driving device 150 drives the clamping element 130 to pivot relative to the fixed frame 120 along a direction D2, the second body 14 is turned over relative to the first body 12. In this way, a situation that a user uses the folding-type electronic device 10 can be simulated. By repeating the above driving operations, rotation times that can be born by the shaft of the folding-type electronic device 10 can be tested.

To avoid a damage of the shaft of the folding-type electronic device 10 due to excessive pivoted angle during the testing process, the testing device 100 of FIG. 1 further includes a limiting switch 170. The limiting switch 170 is, for example, disposed between the clamping element 130 and the fixed frame 120 for outputting a signal to stop an action of the testing device 100 when the pivoted angle of the clamping element 130 relative to the fixed frame 120 along the direction D2 is too large (for example, 180 degrees). Referring to FIG. 1 and FIG. 2, the limiting switch 170 includes a first rod 172, a second rod 174, a first switching element 176 and a second switching element 178. The first rod 172 and the second rod 174 are all fixed to the clamping element 130, and the first switching element 176 and the second switching element 178 are all pivotally connected to the fixed frame 120.

Figure 3C:
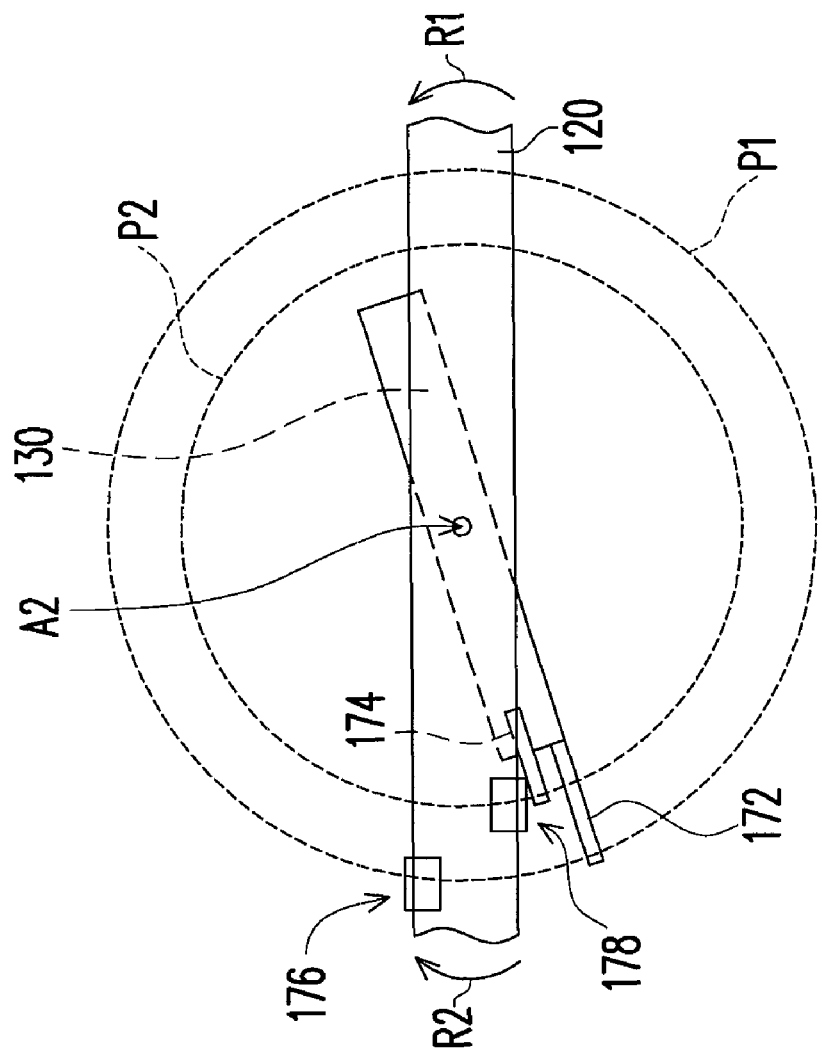

FIGS. 3A-3C are diagrams illustrating partial actions of the testing device of FIG. 1 viewing from a viewing direction V1. A limit for pivoting the second body 14 of the electronic device 10 of FIG. 1 relative to the first body 12 along the second axis A2 is, for example, 180 degrees (i.e. a rotation limit of the clamping element 130 relative to the fixed frame 120 is 180 degrees), and relative positions of the first rod 172, the second rod 174, the first switching element 176 and the second switching element 178 are configured with reference of such limitation.

In detail, when the testing device 100 is in a state shown in FIG. 1, relative positions of the fixed frame 120 and the clamping element 130 are as that shown in FIG. 3A. When the clamping element 130 is rotated for 180 degrees relative to the fixed frame 120 along a direction R1, the second rod 174 is moved along a second moving path P2 to contact with the second switching element 178, so that the second switching element 178 outputs a signal to stop the action of the testing device 100. Similarly, when the clamping element 130 is rotated for 180 degrees relative to the fixed frame 120 along a direction R2, the first rod 172 is moved along a first moving path P1 to contact with the first switching element 176, so that the first switching element 176 outputs a signal to stop the action of the testing device 100.

It should be noticed that when the second rod 174 of FIG. 3A is moved to a position shown in FIG. 3B along the second moving path P2 before contacting with the second switching element 178 as the clamping element 130 is pivoted along the direction R1, the first rod 172 is blocked by the first switching element 176 located on the first moving path P1. Similarly, when the first rod 172 is moved to a position shown in FIG. 3C along the first moving path P1 before contacting with the first switching element 176 as the clamping element 130 is pivoted along the direction R2, the second rod 174 is blocked by the second switching element 178 located on the second moving path P2.

Therefore, the first switching element 176 is pivotally connected to the fixed frame 120, so that when the first rod 172 reaches the position shown in FIG. 3B, it can push away the first switching element 176, so that the second rod 174 can be continually moved along with the clamping element 130 to contact with the second switching element 178. Similarly, the second switching element 178 is pivotally connected to the fixed frame 120, so that when the second rod 174 reaches the position shown in FIG. 3C, it can push away the second switching element 178, so that the first rod 172 can be continually moved along with the clamping element 130 to contact with the first switching element 176. Detailed descriptions are provided below with reference of FIG. 4A and FIG. 4B.

Figure 4B:
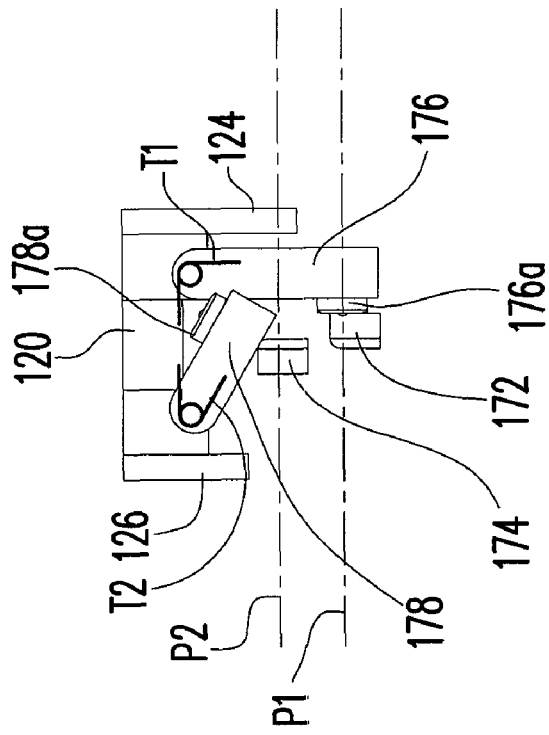
FIG. 4A and FIG. 4B are schematic diagrams illustrating partial actions of a testing device of FIG. 1 viewing from a viewing direction V2.
Figure 4A:
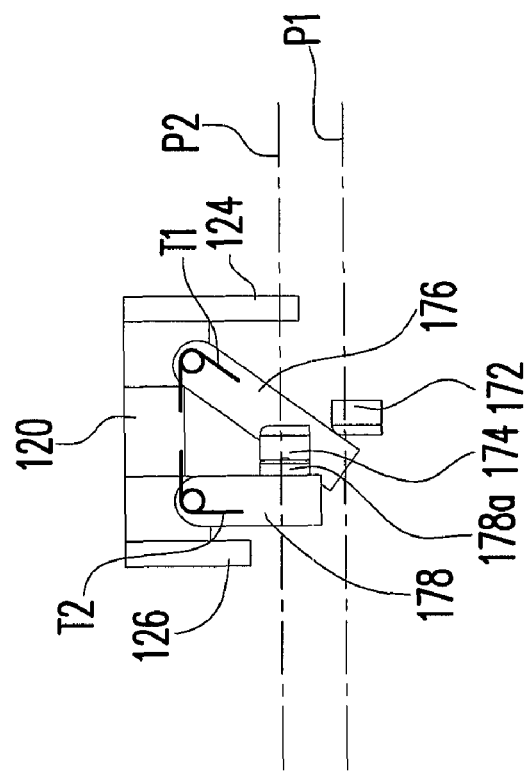

FIG. 4A and FIG. 4B are schematic diagrams illustrating partial actions of the testing device of FIG. 1 viewing from a viewing direction V2. When the first rod 172 is blocked by the first switching element 176 located on the first moving path P1 as that shown in FIG. 3B, the first rod 172 can push the first switching element 176 to pivot relative to the fixed frame 120 as that shown in FIG. 4A, and the first switching element 176 is moved away from the first moving path P1, so that the second rod 174 can be continually moved along with the clamping element 130 to contact with the second switching element 178. Similarly, when the second rod 174 is blocked by the second switching element 178 located on the second moving path P2 as that shown in FIG. 3C, the second rod 174 can push the second switching element 178 to pivot relative to the fixed frame 120 as that shown in FIG. 4B, and the second switching element 178 is moved away from the second moving path P2, so that the first rod 172 can be continually moved along with the clamping element 130 to contact with the first switching element 176.

Referring to FIG. 1, an extending direction of the first rod 172 and an extending direction of the second rod 174 are substantially perpendicular to the second axis A2. A distance L1 between an orthogonal projection of the first rod 172 on a plane A1A2 (a plane defined by the first axis A1 and the second axis A2) and the first axis A1 is less than a distance L2 between an orthogonal projection of the second rod 174 on the plane A1A2 and the first axis A1, and a distance L3 between an orthogonal projection of a free end of the first switching element 176 on the plane A1A2 and the first axis A1 is less than a distance L4 between an orthogonal projection of a free end of the second switching element 178 on the plane A1A2 and the first axis A1. Namely, a position of the first rod 172 in a direction H is lower than a position of the second rod 174 in the direction H, and a position of the free end of the first switching element 176 in the direction H is lower than a position of the free end of the second switching element 178 in the direction H. Moreover, a distance L5 between a free end of the first rod 172 and the second axis A2 is greater than a distance L6 between a free end of the second rod 174 and the second axis A2, and a distance L7 between the first switching element 176 and the second axis A2 is greater than a distance L8 between the second switching element 178 and the second axis A2. In this way, the first rod 172 and the first switching element 176 are all located on the first moving path P1 shown in FIG. 3A, and the second rod 174 and the second switching element 178 are all located on the second moving path P2 shown in FIG. 3A that is different to the first moving path P1, so that when the clamping element 130 is rotated, a miscontact between the first rod element 172 and the second switching element 178 and a miscontact between the second rod element 174 and the first switching element 176 are avoided.

Referring to FIG. 4A and FIG. 4B, in the present exemplary embodiment, the fixed frame 120 has a first blocking wall 124 corresponding to the first switching element 176 and a second blocking wall 126 corresponding to the second switching element 178. After the first rod 172 moves along the first moving path P1 to contact with the first switching element 176 (shown in FIG. 4B), the first rod 172 continually moves along the first moving path P1 to push the first switching element 176 to pivot relative to the fixed frame 120 for leaning against the first blocking wall 124, so that the first rod 172 can assuredly press a button 176a on the first switching element 176. Similarly, after the second rod 174 moves along the second moving path P2 to contact with the second switching element 178 (shown in FIG. 4B), the second rod 174 continually moves along the second moving path P2 to push the second switching element 178 to pivot relative to the fixed frame 120 for leaning against the second blocking wall 126, so that the second rod 174 can assuredly press a button 178a on the second switching element 178.

Moreover, in the present exemplary embodiment, the testing device 100 further includes a first torsion spring T1 and a second torsion spring T2. The first torsion spring T1 is connected to the fixed frame 120 and the first switching element 176 for providing a torque to restore the first switching element 176 pivoted relative to the fixed frame 120 back to the first moving path P1, so that after the first rod 172 is moved away, the first switching element 176 can be restored to its original potion. Similarly, the second torsion spring T2 is connected to the fixed frame 120 and the second switching element 178 for providing a torque to restore the second switching element 178 pivoted relative to the fixed frame 120 back to the second moving path P2, so that after the second rod 174 is moved away, the second switching element 178 can be restored to its original potion.

Other components of the testing device 100 are described in detailed below. Referring to FIG. 1 and FIG. 2, the clamping element 130 may include a support frame 132 and a plurality of clamps 134. The support frame 132 is pivotally connected to the fixed frame 120, and the clamps 134 are used for clamping the second body 14. In the present exemplary embodiment, the support frame 132 may include a frame body 132a and a lifter 132b. The frame body 132a is pivotally connected to the fixed frame 120. The lifter 132b is liftably disposed on the frame body 132a, which can be adjusted upwards or downwards according to a size of the second body 14. Moreover, the support frame 132 further includes a plurality of fixing screws 132c, which are used for fixing a relative position between the lifter 132ba and the frame body 132a after the lifter 132b is adjusted to a desired position.

Furthermore, the clamps 134 can be axially connected to the lifter 132b of the support frame 132, and the clamping element 130 can further include a plurality of elastic elements 136. The elastic elements 136 are respectively disposed on the clamps 134. The elastic elements 136 are respectively located between the lifter 132b and the clamps 134 for exerting elastic forces to the second body 14 through the clamps 134. In the present exemplary embodiment, the elastic elements 136 can be springs with different elastic coefficients, so as to simulate an operation state of a user holding the second body 14. In this way, such test can be more close to an actual utilization state.

Moreover, the testing device 100 may further include a plurality of fixing elements 160, which are detachably connected between the fixed frame 120 and the clamping element 130 for limiting a pivotal rotation of the clamping element 130 relative to the fixed frame 120. In the present exemplary embodiment, the fixing elements 160 are, for example, screws. When the fixing elements 160 are locked between the fixed frame 120 and the clamping element 130 (as that shown in FIG. 1), a pivotal rotation of the second body 14 relative to the first boy 12 along the second axis A2 is prevented. Namely, the testing device 100 can also only test the opening and closing operations of the folding-type electronic device 10 along a single axial direction as that does of the conventional art. Comparatively, when the fixing elements 160 are detached (as that shown in FIG. 2), the testing device 100 can test the opening and closing operations and a turning over operation of the folding-type electronic device 10 along two axial directions of the first axis A1 and the second axis A2.

Figure 5:
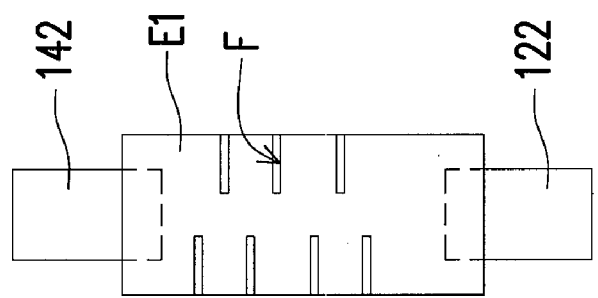
FIG. 5 is a schematic diagram illustrating a coupling of FIG. 1.

Moreover, the testing device 100 further includes two couplings E1 and E2, which are flexibly connected to the first driving device 140 and the second driving device 150, respectively. FIG. 5 is a schematic diagram illustrating a coupling of FIG. 1. Referring to FIG. 1 and FIG. 5, taking the coupling E1 as an example, the coupling E1 is connected between a shaft 142 of the first driving device 140 and a shaft 122 of the fixed frame 120. The coupling E1 may have a plurality of holes F, which allow a slight bending of the coupling E1 for absorbing an alignment error between the shafts 142 and 122.

Figure 6:
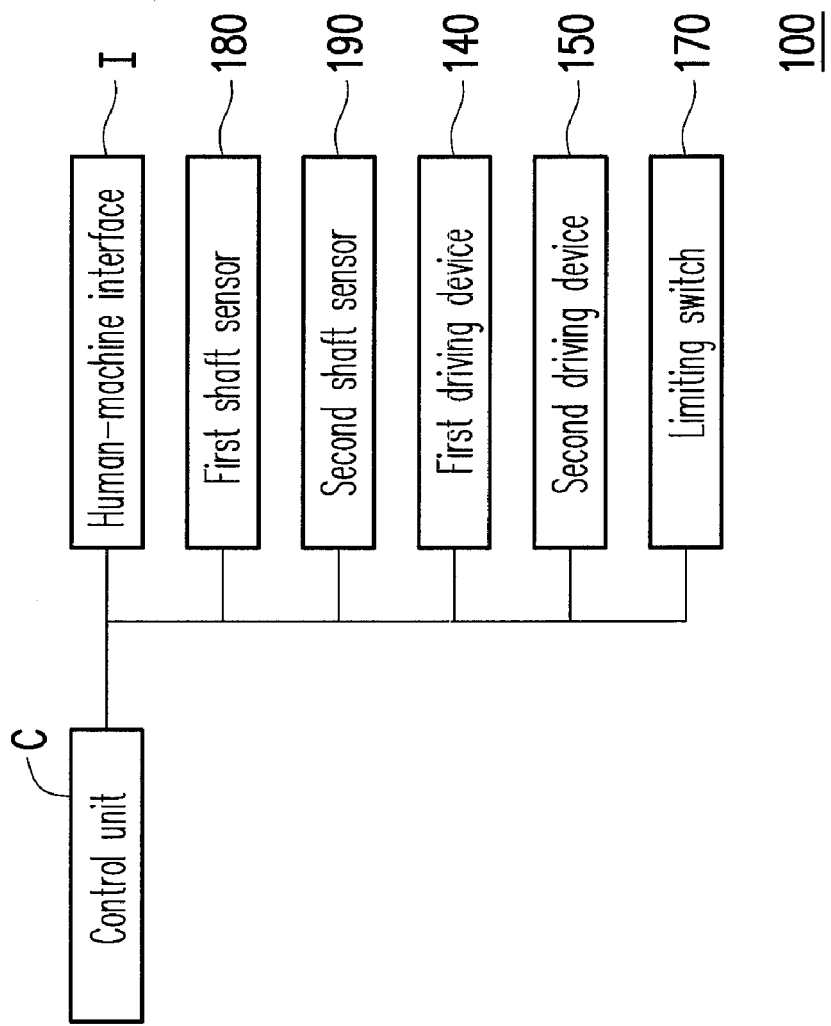
FIG. 6 is a circuit block diagram of a testing device of FIG. 1.

FIG. 6 is a circuit block diagram of the testing device of FIG. 1. Referring to FIG. 1 and FIG. 6, the testing device 100 may further include a first shaft sensor 180, a second shaft sensor 190 and a control unit C. The first shaft sensor 180 is disposed between the carrier platform 110 and the fixed frame 120 for sensing a first pivoted angle of the fixed frame 120 relative to the carrier platform 110 along the direction D1. The second shaft sensor 190 is disposed between the clamping element 130 and the fixed frame 120 for sensing a second pivoted angle of the clamping element 130 relative to the fixed frame 120 along the direction D2. The control unit C is coupled to the first driving device 140, the second driving device 150, the first shaft sensor 180 and the second shaft sensor 190. The control unit C is used for controlling the first driving device 140 and the second driving device 150 according to the first pivoted angle and the second pivoted angle.

Moreover, the control unit C is also coupled to the first switching element 176 and the second switching element 178. When the first rod 172 contacts with the first switching element 176 (shown in FIG. 4B), the first switching element 176 outputs a switch signal to the control unit C, so as to stop the action of the first driving device 140. When the second rod 174 contacts with the second switching element 178 (shown in FIG. 4A), the second switching element 178 outputs a switch signal to the control unit C, so as to stop the action of the first driving device 140.

Figure 7:
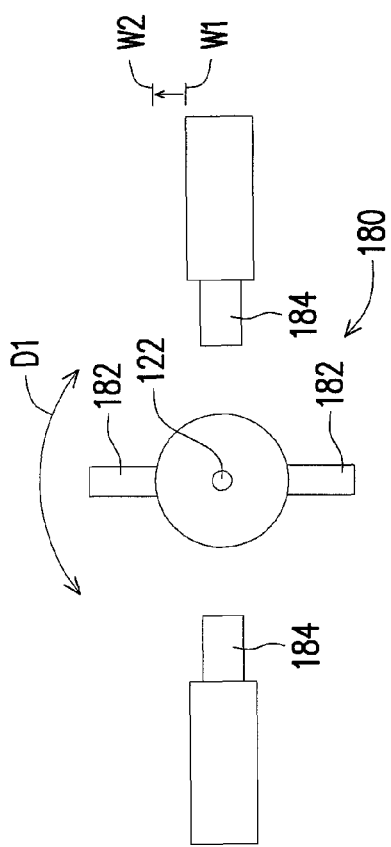
FIG. 7 is a schematic diagram illustrating a first shaft sensor of FIG. 1.

FIG. 7 is a schematic diagram illustrating the first shaft sensor of FIG. 1. Referring to FIG. 1 and FIG. 7, the first shaft sensor 180 of the testing device 100 can be a magnetic inductive shaft sensor. The first shaft sensor 180 may include two magnetic devices 182, two magnetic-induction devices 184 and a turntable 186. The two magnetic devices 182 are connected to the turntable 186, and the two magnetic-induction devices 184 are respectively disposed at two sides of the turntable 186. When the turntable 186 is rotated along with the shaft 122 of the fixed frame 120, the turntable 186 drives the two magnetic devices 182 to rotate. When the two magnetic devices 182 are rotated to respectively close to the two magnetic-induction devices 184, the two magnetic-induction devices 184 send a signal to the control unit C to represent that the first driving device 140 has been pivoted for the first pivoted angle.

In the present exemplary embodiment, the user can adjust up and down positions of the two magnetic-induction devices 184 relative to the turntable 186, so as to determine a magnitude of the first pivoted angle. For example, when the two magnetic-induction devices 184 are moved upwards from a position W1 to a position W2, since the two magnetic-induction devices 184 can induct a magnetic variation when the two magnetic devices 182 only rotate for a small range, the magnitude of the first pivoted angle is reduced.

Figure 8:
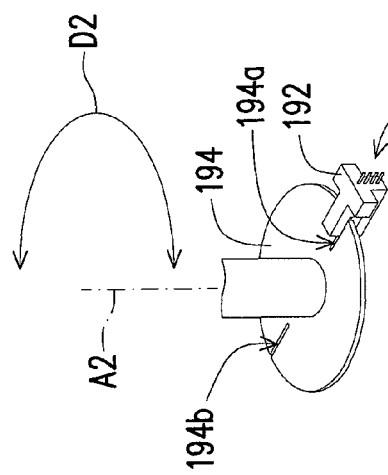
FIG. 8 is a schematic diagram illustrating a second shaft sensor of FIG. 1.

FIG. 8 is a schematic diagram illustrating the second shaft sensor of FIG. 1. Referring to FIG. 1 and FIG. 8, the second shaft sensor 190 of the testing device 100 can be a gap-inductive shaft sensor. The second shaft sensor 190 may include a sensing device 192 and a turntable 194. The turntable 194 has a first gap 194a and a second gap 194b, and an angle difference between the first gap 194a and the second gap 194b is 180 degrees. The sensing device 192 and the turntable 194 are respectively fixed on the fixed frame 120 and the clamping element 130. When the second driving device 150 drive the clamping element 130 to rotate relative to the fixed frame 120, the clamping element 130 drives the turntable 194 to rotate relative to the sensing device 192.

When the sensing device 192 is aligned to the first gap 194a (shown as a state of FIG. 8), the sensing device 192 sends a detecting signal to the control unit C. When the turntable 194 is continually rotated to align the second gap 194b with the sensing device 192, the sensing device 192 sends another detecting signal to the control unit C. After the control unit C receives two consecutive detecting signals, it is determined that the clamping element 130 has been pivoted relative to the fixed frame 120 for the second pivoted angle (for example, 180 degrees, i.e. the angle difference between the first gap 194a and the second gap 194b). In the present exemplary embodiment, the user can adjust a number of the gaps and angle differences of the gaps according to an actual design requirement.

Moreover, in another exemplary embodiment that is not illustrated, the first shaft sensor 180 and the second shaft sensor 190 can all be magnetic inductive shaft sensors or gap-inductive shaft sensors, which are not limited by the invention.

A testing flow is described in detail with reference of FIG. 1, FIG. 2 and FIG. 6. The testing device 100 can further include a human-machine interface I, so that the user can input testing conditions such as start time, stop time, opening/closing angle, turning over angle, testing times, etc. through the human-machine interface I. After the above settings are completed, the first shaft sensor 180 and the second shaft sensor 190 can be correspondingly adjusted, so that the first pivoted angle and the second pivoted angle can be in accordance with the testing conditions (for example, 90 degrees and 180 degrees). Then, the user can press a start button (not shown) to start the testing process.

First, the control unit C drives the first driving device 140 to rotate forwards (a clockwise direction of FIG. 2) along the first axis A1 according to the opening/closing angle (for example, greater than 90 degrees and less than 180 degrees) set by the user, so as to drive the fixed frame 120 to pivot relative to the carrier platform 110, so that the second body 14 originally covering the first body 12 is opened for more than the first pivoted angle 90 degrees (shown as a state of FIG. 1). Now, the first shaft sensor 180 outputs a signal to the control unit C, and the control unit C activates the second driving device 150.

Then, the second driving device 150 drives the clamping element 130 to rotate backwards (an anticlockwise direction of FIG. 2) relative to the fixed frame 120 along the second axis A2, so as to turn over the second body 14 relative to the first body 12 (shown as a state of FIG. 2) until a display area of the second body 14 is turned over to the back. When the second shaft sensor 190 detects that the clamping element 130 is pivoted relative to the fixed frame 120 for the second pivoted angle (180 degrees), the control unit C continually activates the first driving device 140. Now, the first driving device 140 is rotate backwards (the anticlockwise direction of FIG. 2) along the first axis A1 to drive the second body 14 to cover on the first body 12, so that the display area of the second body 14 is turned upwards.

Then, the control unit C stops the operation of the first driving device 140 for a predetermined time according to the testing condition. After the operation of the first driving device 140 is stopped for the predetermined time, the control unit C drives the first driving device 140 to rotate forwards, so that the second body 14 is opened relative to the first body 12. When the first shaft sensor 180 detects that the second body 14 is pivoted for the first pivoted angle (90 degrees), the control unit C receives a signal from the first shaft sensor 180, and drives the second driving device 150 to rotate forwards (the clockwise direction of FIG. 2).

Then, when the display area of the second body 14 is returned back to the front side, namely, the second shaft sensor 190 detects that the second body 14 is pivoted for the second pivoted angle 180 degrees, the control unit C again drives the first driving device 140 to rotate backwards along the first axis A1, so as to drive the second body 14 to cover on the first body 12, and now one testing process is completed.

Then, according to the testing conditions, the above testing process is repeated for a desired testing times. It should be noticed that the limiting switch 170 (shown in FIG. 1) can forcibly stop the operation of the testing device 100 in case of malfunction or failure of the second shaft sensor 190, so as to avoid a damage of the electronic device 10 caused by excessive pivotal rotation thereof due to continuous operation of the testing device 100.

Moreover, in the present exemplary embodiment, by extending the fixed frame 120 and applying another set of second driving device 150', the testing device 100 can simultaneously test the folding-type electronic device 10 and another folding-type electronic device 10'. In another exemplary embodiment that is not illustrated, the single folding-type electronic device 10 can be tested, and more than three folding-type electronic devices can also be simultaneously tested, which is not limited by the invention.

In summary, during the testing process of the testing device of the invention, the operation of the testing device can be stopped through a contact between the first rod and the first switching element of the limiting switch or a contact between the second rod and the second switching element, so as to avoid a damage of the shaft of the folding-type electronic device caused by excessive pivoted angle during the testing process. Moreover, the first switching element and the second switching element are pivotally connected to the fixed frame. In this way, when the first rod cannot be moved to contact the first switching element due to that the second switching element blocks the second rod, the second rod can temporarily push away the second switching element, so that the first rod can be moved to contact with the first switching element. Similarly, when the second rod cannot be moved to contact the second switching element due to that the first switching element blocks the first rod, the first rod can temporarily push away the first switching element, so that the second rod can be moved to contact with the second switching element. Moreover, torsion springs can be used to provide torques to restore the first switching element and the second switching element, so as to further ensure a correctness of the operation of the limiting switch.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A testing device, adapted to test an electronic device, the electronic device having a first body and a second body, and the first body being suitable for rotating relative to the second body, the testing device comprising:

a carrier platform, for carrying the first body;
a fixed frame, pivotally connected to the carrier platform;
a clamping element, pivotally connected to the fixed frame, for clamping the second body;
a limiting switch, comprising:
    a first rod, fixed to the clamping element;
    a second rod, fixed to the clamping element;
    a first switching element, pivotally connected to the fixed frame and located on a first moving path; and
    a second switching element, pivotally connected to the fixed frame and located on a second moving path, wherein when the clamping element is pivoted relative to the fixed frame along a first direction, the second switching element is pushed by the second rod to pivot relative to the fixed frame and move away from the second moving path, and the first rod is moved along the first moving path to contact with the first switching element, and when the clamping element is pivoted relative to the fixed frame along a second direction opposite to the first direction, the first switching element is pushed by the first rod to pivot relative to the fixed frame and move away from the first moving path, and the second rod is moved along the second moving path to contact with the second switching element.

2. The testing device as claimed in claim 1, further comprising:
a first driving device, disposed between the carrier platform and the fixed frame, for driving the fixed frame to pivot relative to the carrier platform; and
a second driving device, disposed between the clamping element and the fixed frame, for driving the clamping element to pivot relative to the fixed frame.

3. The testing device as claimed in claim 2, further comprising:
a first shaft sensor, disposed between the carrier platform and the fixed frame, for sensing a first pivoted angle of the fixed frame relative to the carrier platform;
a second shaft sensor, disposed between the clamping element and the fixed frame, for sensing a second pivoted angle of the clamping element relative to the fixed frame;
a control unit, coupled to the first driving device, the second driving device, the first shaft sensor and the second shaft sensor, for controlling the first driving device and the second driving device according to the first pivoted angle and the second pivoted angle; and
two couplings, flexibly connected to the first driving device and the second driving device, respectively,
when the first rod contacts with the first switching element, the first switching element outputs a first switch signal to the control unit for stopping an action of the first driving device, and when the second rod contacts with the second switching element, the second switching element outputs a second switch signal to the control unit for stopping an action of the first driving device.

4. The testing device as claimed in claim 1, wherein the clamping element comprises:
a support frame, pivotally connected to the fixed frame; and
a plurality of clamps, connected to the support frame, for clamping the second body.

5. The testing device as claimed in claim 4, wherein the support frame comprises:
a frame body, pivotally connected to the fixed frame; and
a lifter, liftably disposed on the frame body, and the clamps being connected to the lifter.

6. The testing device as claimed in claim 4, wherein the clamps are axially disposed on the support frame, and the clamping element further comprises:
a plurality of elastic elements, disposed on the clamps, for exerting an elastic force to the second body through the clamps.

7. The testing device as claimed in claim 1, further comprising:
a plurality of fixing elements, detachably connected between the fixed frame and the clamping element, for limiting a pivotal rotation of the clamping element relative to the fixed frame.

8. The testing device as claimed in claim 1, wherein the fixed frame is pivotally connected to the carrier platform along a first axis, the clamping element is pivotally connected to the fixed frame along a second axis, and the first axis is substantially perpendicular to the second axis.

9. The testing device as claimed in claim 8, wherein an extending direction of the first rod and an extending direction of the second rod are substantially perpendicular to the second axis, a distance between a free end of the first rod and the second axis is greater than a distance between a free end of the second rod and the second axis, and a distance between the first switching element and the second axis is greater than a distance between the second switching element and the second axis.

10. The testing device as claimed in claim 1, wherein the first axis and the second axis define a plane, a distance between an orthogonal projection of the first rod on the plane and the first axis is less than a distance between an orthogonal projection of the second rod on the plane and the first axis, and a distance between an orthogonal projection of a free end of the first switching element on the plane and the first axis is less than a distance between an orthogonal projection of a free end of the second switching element on the plane and the first axis.

11. The testing device as claimed in claim 1, wherein the fixed frame has a first blocking wall corresponding to the first switching element, and after the first rod moves along the first moving path to contact with the first switching element, the first rod continually moves along the first moving path to push the first switching element to pivot relative to the fixed frame for contacting with the first blocking wall.

12. The testing device as claimed in claim 11, wherein the fixed frame has a second blocking wall corresponding to the second switching element, and after the second rod moves along the second moving path to contact with the second switching element, the second rod continually moves along the second moving path to push the second switching element to pivot relative to the fixed frame for contacting with the second blocking wall.

13. The testing device as claimed in claim 1, further comprising:
a first torsion spring connected to the fixed frame and the first switching element for providing a torque to restore the first switching element pivoted relative to the fixed frame back to the first moving path; and
a second torsion spring connected to the fixed frame and the second switching element for providing a torque to restore the second switching element pivoted relative to the fixed frame back to the second moving path.

14. A limiting switch, adapted to a testing device, the testing device comprising a carrier platform, a fixed frame and a clamping element, the fixed frame being pivotally connected to the carrier platform, and the clamping element being pivotally connected to the fixed frame, the limiting switch comprising:
a first rod, fixed to the clamping element;
a second rod, fixed to the clamping element;
a first switching element, pivotally connected to the fixed frame and located on a first moving path; and
a second switching element, pivotally connected to the fixed frame and located on a second moving path, wherein when the clamping element is pivoted relative to the fixed frame along a first direction, the second switching element is pushed by the second rod to pivot relative to the fixed frame and move away from the second moving path, and the first rod is moved along the first moving path to contact with the first switching element, and when the clamping element is pivoted relative to the fixed frame along a second direction opposite to the first direction, the first switching element is pushed by the first rod to pivot relative to the fixed frame and move away from the first moving path, and the second rod is moved along the second moving path to contact with the second switching element.

15. The limiting switch as claimed in claim 14, wherein a control unit of the testing device is coupled to the first switching element and the second switching element, wherein when the first rod contacts with the first switching element, the first switching element outputs a first switch signal to the control unit for stopping an action of the first driving device, and when the second rod contacts with the second switching element, the second switching element outputs a second switch signal to the control unit for stopping an action of the first driving device.

16. The limiting switch as claimed in claim 14, wherein the fixed frame is pivotally connected to the carrier platform along a first axis, the clamping element is pivotally connected to the fixed frame along a second axis, and the first axis is substantially perpendicular to the second axis, an extending direction of the first rod and an extending direction of the second rod are substantially perpendicular to the second axis, a distance between a free end of the first rod and the second axis is greater than a distance between a free end of the second rod and the second axis, and a distance between the first switching element and the second axis is greater than a distance between the second switching element and the second axis.

17. The limiting switch as claimed in claim 16, wherein the first axis and the second axis define a plane, a distance between an orthogonal projection of the first rod on the plane and the first axis is less than a distance between an orthogonal projection of the second rod on the plane and the first axis, and a distance between an orthogonal projection of a free end of the first switching element on the plane and the first axis is less than a distance between an orthogonal projection of a free end of the second switching element on the plane and the first axis.

18. The limiting switch as claimed in claim 14, wherein the fixed frame has a first blocking wall corresponding to the first switching element, and after the first rod moves along the first moving path to contact with the first switching element, the first rod continually moves along the first moving path to push the first switching element to pivot relative to the fixed frame for contacting with the first blocking wall.

19. The limiting switch as claimed in claim 18, wherein the fixed frame has a second blocking wall corresponding to the second switching element, and after the second rod moves along the second moving path to contact with the second switching element, the second rod continually moves along the second moving path to push the second switching element to pivot relative to the fixed frame for contacting with the second blocking wall.

20. The limiting switch as claimed in claim 14, wherein the testing device further comprises:
a first torsion spring connected to the fixed frame and the first switching element for providing a torque to restore the first switching element pivoted relative to the fixed frame back to the first moving path; and
a second torsion spring connected to the fixed frame and the second switching element for providing a torque to restore the second switching element pivoted relative to the fixed frame back to the second moving path.

* * * * *